(12) United States Patent
Halberthal et al.

(10) Patent No.: US 9,289,943 B2
(45) Date of Patent: Mar. 22, 2016

(54) APPARATUS AND METHOD FOR ATTACHING AN RF TAG TO A SPONGE ITEM

(75) Inventors: Reuven Halberthal, Tzur Igal (IL); Jacob Poremba, Nes Ziona (IL)

(73) Assignee: Haldor Advanced Technologies L.T.D, Hod Hasharon (IL)

( * ) Notice: Subject to any disclaimer, the term of this patent is extended or adjusted under 35 U.S.C. 154(b) by 210 days.

(21) Appl. No.: 13/814,737

(22) PCT Filed: Aug. 2, 2011

(86) PCT No.: PCT/IL2011/000625
§ 371 (c)(1),
(2), (4) Date: Apr. 9, 2013

(87) PCT Pub. No.: WO2012/020399
PCT Pub. Date: Feb. 16, 2012

(65) Prior Publication Data
US 2013/0199720 A1 Aug. 8, 2013

Related U.S. Application Data

(63) Continuation-in-part of application No. 12/852,525, filed on Aug. 9, 2010, now abandoned.

(51) Int. Cl.
| | |
|---|---|
| *B29C 65/14* | (2006.01) |
| *A61B 19/00* | (2006.01) |
| *A61F 13/44* | (2006.01) |
| *A61B 17/00* | (2006.01) |

(52) U.S. Cl.
CPC ............ *B29C 65/1406* (2013.01); *A61B 19/44* (2013.01); *A61F 13/44* (2013.01); *A61B 2017/005* (2013.01); *A61B 2017/00526* (2013.01); *A61B 2019/448* (2013.01); *A61B 2019/4826* (2013.01)

(58) Field of Classification Search
CPC .... B29C 65/1406; A61B 19/44; A61B 13/44; A61B 2019/448
USPC ................. 156/272.2, 275.5, 379.6, 380.8
See application file for complete search history.

(56) References Cited

U.S. PATENT DOCUMENTS

| | | | | |
|---|---|---|---|---|
| 5,518,569 | A * | 5/1996 | Achilles et al. | 156/250 |
| 6,026,818 | A | 2/2000 | Blair et al. | |
| 6,406,151 | B1 * | 6/2002 | Fujimori | 353/119 |
| 6,604,342 | B1 * | 8/2003 | Appelbaum | 53/471 |
| 2002/0185212 | A1 * | 12/2002 | Schaupp et al. | 156/205 |
| 2004/0010263 | A1 * | 1/2004 | Boucher et al. | 606/99 |
| 2004/0200566 | A1 * | 10/2004 | Bellafore et al. | 156/230 |
| 2004/0226659 | A1 * | 11/2004 | Denholm et al. | 156/556 |
| 2005/0049564 | A1 * | 3/2005 | Fabian | 604/362 |
| 2006/0106368 | A1 * | 5/2006 | Miller et al. | 606/1 |

(Continued)

FOREIGN PATENT DOCUMENTS

| | | |
|---|---|---|
| EP | 1804203 | 7/2007 |
| GB | 2472025 | 1/2011 |

*Primary Examiner* — Daniel McNally
(74) *Attorney, Agent, or Firm* — Soroker—Agmon

(57) ABSTRACT

The subject matter discloses a method of attaching a tag to a disposable item such as a sponge, the method comprising obtaining a tag and a disposable item; attaching the tag to the disposable item using an adhesive material. The adhesive material is cured by ultraviolet radiation. The method also comprises applying the ultraviolet radiation on the tag attached on the disposable item. The tag may be an RE tag.

12 Claims, 3 Drawing Sheets

(56) References Cited

U.S. PATENT DOCUMENTS

2006/0232407 A1* 10/2006 Ballard .................. A61B 19/44
340/572.1
2007/0139203 A1* 6/2007 Ishikawa et al. ........... 340/572.8
2007/0150219 A1* 6/2007 Cawker et al. .................. 702/82
2008/0024278 A1* 1/2008 Volpi et al. .................... 340/10.1
2009/0212913 A1 8/2009 Barksdale et al.

* cited by examiner

APPARATUS AND METHOD FOR ATTACHING AN RF TAG TO A SPONGE ITEM

RELATED APPLICATIONS

This application claims priority as a national stage of PCT application No: PCT/IL2011/000625 filed on Aug. 2, 2011 and published as WO 2012/020399. The PCT application claims priority as a continuation in part of U.S. application Ser. No. 12/852,525 filed on Aug. 9, 2010 the disclosure of which is incorporated herein by reference.

BACKGROUND OF THE INVENTION

1. Field of the Invention

The present invention relates to attaching RE tags in general and to attaching RF tags to a sponge and gauze item in particular.

2. Discussion of the Related Art

There are many environments in which multiple tools and disposables are used, including for example operation rooms, hangars, garages, or the like.

An operation room is a facility in which intrusive operations are performed on patients. Typically, multiple people participate in an operation, using multiple tools, such as scalpels, forceps, and others, varying according to the surgery being performed.

Intensive efforts are invested in keeping track of all tools and disposables, in order to make sure no tool unintentionally remains inside the patient's body. Therefore, careful counting is performed before, during and after the operation. Counting the tools is a tedious job and requires intensive resources, including mental resources, personnel time and down-time of the operating room. Counting the tools towards the end of an operation also increases the time the patient's body is open with the associated risks, in addition, counting is not always error-free, and in too many cases tools end up being left within the patient's body, causing severe damages and even death.

One of the elements counted in an operation room is sponge items, such as gauze and laparotomy sponges. It is also desired to count the sponge items after an operation to verify that none is left in the patient's tissues. Counting the sponge items can be performed by detecting X-ray detectable wires attached to the sponge items using an X-ray machine, Such machine generates radiation and cannot distinguish one sponge item from several items. As a result, after removing a sponge item from the patient's tissue, one still cannot verify that the patient's tissue is free from sponge items unless rescanning the patient again with X-ray machine.

To solve the above problem, RE tags may be attached to sponge items by sewing. The sewing may be performed manually, which is not cost-effective and time consuming. Manual sewing reduces the throughput of the attaching process and increases the costs of the machine that outputs the sponges from raw sheet of the sponge material. It is challenging to mechanize the sewing process, as there are many sizes and models of sponge items, on which the RE tags are to be attached. For example, a different machine is required for sewing an RE tag to a 30 cm long sponge than for a 45 cm long sponge.

There is thus a need in the art for a biocompatible and sterilization-resistant identification tag to be attached to a sponge, and a automated cost effective method for attaching the tag to the sponge.

SUMMARY OF THE PRESENT INVENTION

The subject matter discloses a method of attaching a tag to a sponge item, the method comprising obtaining a tag, obtaining a sponge item and attaching the tag to the disposable item using an adhesive material. The adhesive material is cured by ultraviolet radiation. The method further comprises applying the ultraviolet radiation on the tag attached on the disposable item.

In some cases, the tag is an RE tag. In some cases, the adhesive material is attached to the tag before the tag is attached to the disposable item. In some cases, the adhesive material is attached to the disposable item before the tag is attached to the disposable item.

In some cases, the method further comprises a step of folding the disposable item. In some cases, the adhesive material is attached to more than one layer of the folded disposable item. In some cases, the ultraviolet radiation cures the adhesive material in more than one layer of the folded disposable item.

In some cases, the step of attaching is performed before folding the disposable item. In some cases, the method further comprises a step of maneuvering the tag from tag storage to a working plate on which the disposable item is mounted. Optionally, the adhesive material is DYMAX Ultra Light-Weld 204-CTH-F.

The subject matter also discloses a system for attaching a tag to a sponge item, the system comprising a maneuvering mechanism for maneuvering the tag towards the sponge item and an adhesive material storage unit for providing adhesive material attaching the tag and the sponge item. The system also comprises an ultraviolet radiation module for radiating ultraviolet radiation on the tag attached to the sponge item; wherein the ultraviolet radiation cures the adhesive material.

In some cases, the maneuvering mechanism maneuvers the tag to the adhesive material storage unit before mounting the tag on the sponge item.

BRIEF DESCRIPTION

Exemplary non-limited embodiments of the disclosed subject matter will be described, with reference to the following description of the embodiments, in conjunction with the figures. The figures are generally not shown to scale and any sizes are only meant to be exemplary and not necessarily limiting. Corresponding or like elements are optionally designated by the same numerals or letters.

DETAILED DESCRIPTION OF EXEMPLARY EMBODIMENTS

One technical challenge disclosed in the subject matter is to attach a tag to a sponge item while maintaining sterilization requirements, such as used in medical environments and hospitals.

One technical solution of the disclosed subject matter is a system and a method for attaching a tag to a sponge item. The tag can be an RF tag. The method comprises receiving a sponge item from a storage and mounting the sponge item on a working plate. The method further comprises receiving a tag to be soaked in a UV adhesive material and placed on the sponge item and placing the tag on the sponge item. The method also comprises a step of drying an adhesive material, attaching the tag to the disposable item. The drying is performed using Ultraviolet light emitted from a UV emitter.

Figure 1:
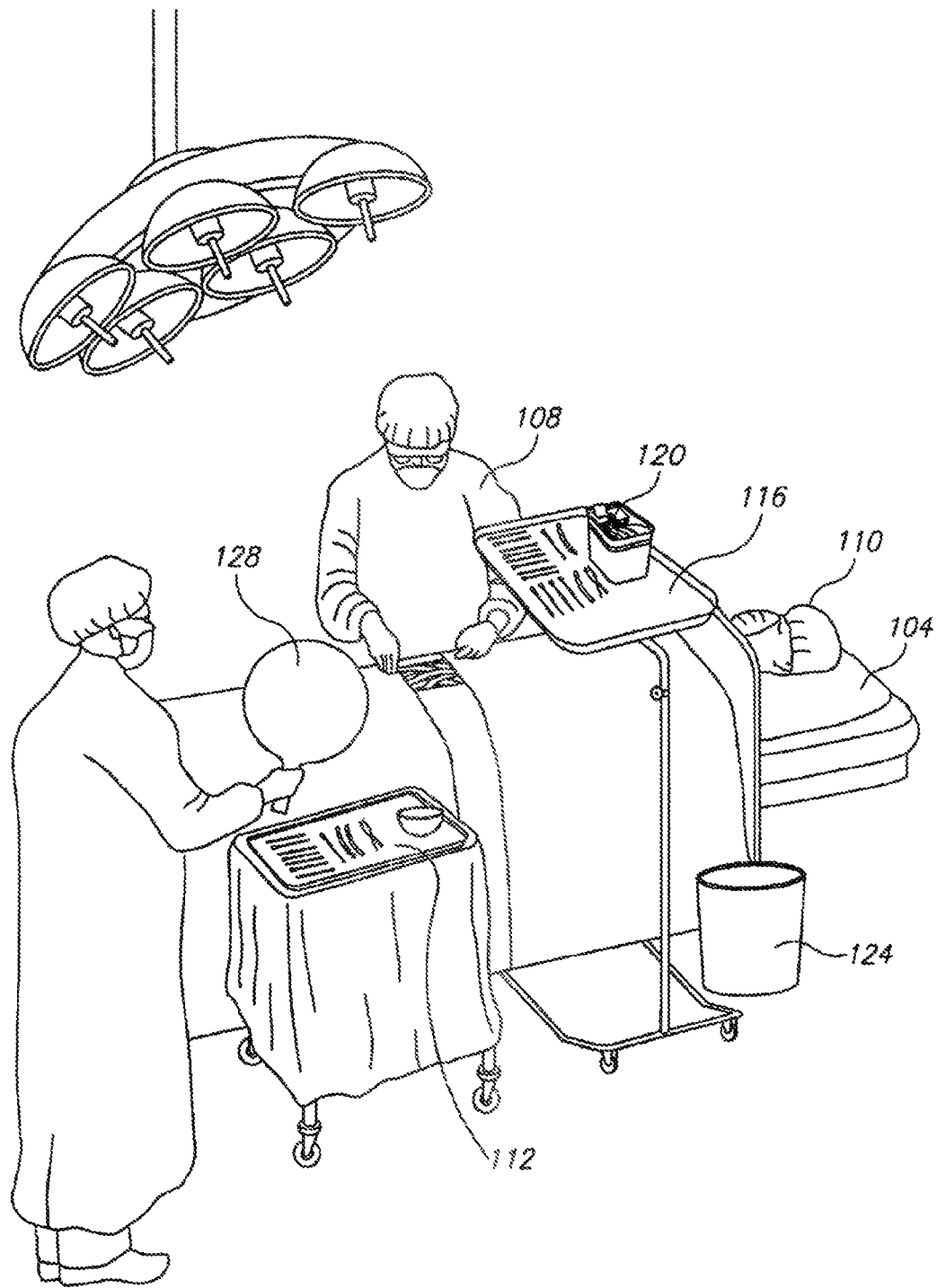
FIG. 1 shows a schematic illustration of an operation room, in which an identification and tracking system and method are required, according to exemplary embodiments of the subject matter.

FIG. 1 shows a schematic illustration of an operation room, in which an identification and tracking system and method are required.

A typical operation room comprises an operation bed 104 on which a patient 110 being operated on lies. A surgeon 108 stands by patient 110 and operates on him, A circulating nurse who does not touch the sponges but only opens their wraps may place the sponges on instrument table 112. Surgeon 108 receives the sponges as required from a scrub nurse who takes the sponges from an instrument table 112.

Surgeon 108 or another team member can place the sponges on a moveable tray 116 placed above or near the patient 110, often called a Mayo. Each operation room typically has one or more instrument tables and one or more Mayos, depending on factors such as the complexity of the surgery, number of surgeons and other team members, personal preferences or others.

The team members retrieve clean sponges from one or more clean sponge bins or dispenser 120, and throw the used ones into one or more waste buckets 124.

Thus, at the end of the surgery, all sponges that were in the operation room prior to the surgery, should be on instrument table 112, on Mayo 116, in clean sponge bin 120 or in waste bucket 124 (collectively referred to as the "utilities").

The operation room is also equipped with a wand 128, which is also an antenna, and which is used for identifying and tracking items within the body of patient 110, by waving the wand near patient 110.

Figure 2:
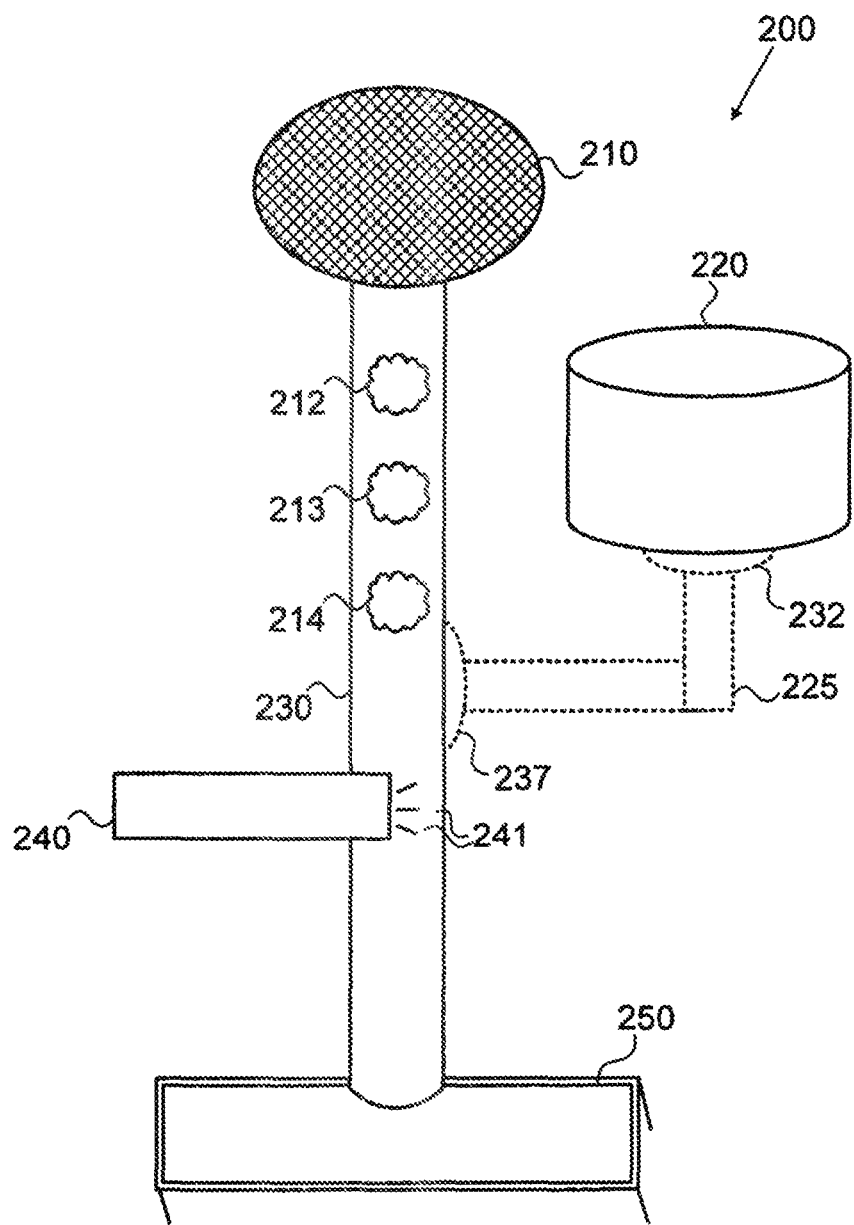
FIG. 2 shows a top view of a production line environment for attaching a tag to a disposable item, according to exemplary embodiments of the subject matter.

FIG. 2 shows a top view of a production line environment 200 for attaching a tag to a disposable item, according to exemplary embodiments of the subject matter. The environment 200 comprises a tag storage 220 for storing one or more tags to be attached to disposable items.

The environment 200 further comprises a disposable item storage 210 for storing disposable items. The disposable items may also be provided directly from a manufacturing machine or a production line of disposable items, which may be regarded as equivalent to the disposable item storage 210. The disposable item may be of one or more types, such as sponges, or cotton wool items. The disposable item may be a gauze pad, a laparotomy sponge and the like. The disposable item storage 210 may comprise two or more storage units for storing two or more types of disposable items.

The tag storage 220 may store the tags arranged in a tag stack. The tag storage 220 may comprise a mechanism for outputting one or more tags every predefined period, for example for 2 disposable items every 10 seconds.

The environment 200 may further comprise a working plate 230 on which the tag is attached to the disposable item. The working plate 230 may be a conveyor belt. The working plate 230 may be positioned between the disposable item storage 210 and an endpoint 250 to which the disposable items with an attached tag are provided. Optionally, disposable items are released from disposable item storage 210 and conveyed along working plate 230 to endpoint 250.

The environment 200 may further comprise a maneuvering mechanism 225 for maneuvering tags from the tag storage 220 to meet disposable items such as 212, 213, and 214 as they are being conveyed along working plate 230. Optionally, tag storage 220 has a tag release interface 232 that provides tags from tag storage 220 to maneuvering mechanism 225. Optionally, the maneuvering mechanism 225 moves tags from tag release interface 232, wherein the maneuver mechanism 225 obtains a tag, to a disposable item interface 237, wherein the maneuvering mechanism 225 delivers the tags to be mounted on the disposable item. The maneuvering mechanism 225 may contain one or more gripping arms (not shown) to receive the tag from the tag storage 220.

The tag is attached to the disposable item using an adhesive material that is UV curable. The adhesive material may be provided on the tag before or after the tag is obtained from the maneuvering mechanism 225. The adhesive material can be provided on the disposable item before attachment to the tag. The UV curable adhesive material may be DYMAX Ultra Light-Weld 204-CTH-F.

In an exemplary embodiment of the disclosed subject matter, the maneuvering mechanism 225 grips a tag, maneuvers the tag to a dispensing area of an adhesive material storage and places the tag containing the adhesive material on the disposable item. In some cases, the adhesive material is obtained only on one side of the tag, the side attached to the disposable item.

The disposable items such as 212, 213, and 214 may be positioned on the working plate 230 when the tags are mounted thereon. The disposable items may be folded in order to reduce the volume or surface area they consume. Attaching the tags may be done before folding or after.

The environment 200 further comprises an ultraviolet (UV) emitting device 240. The UV emitting device 240 emits UV radiation 241 on the tag attached to the disposable item as it passes by. The UV radiation 241 cures the adhesive material. The adhesive material is adapted to be cured by the UV radiation 241. The UV radiation 241 may be applied on a predefined area on the working plate 230 or applied generally to the direction of the tag attached to the disposable item.

Figure 3:
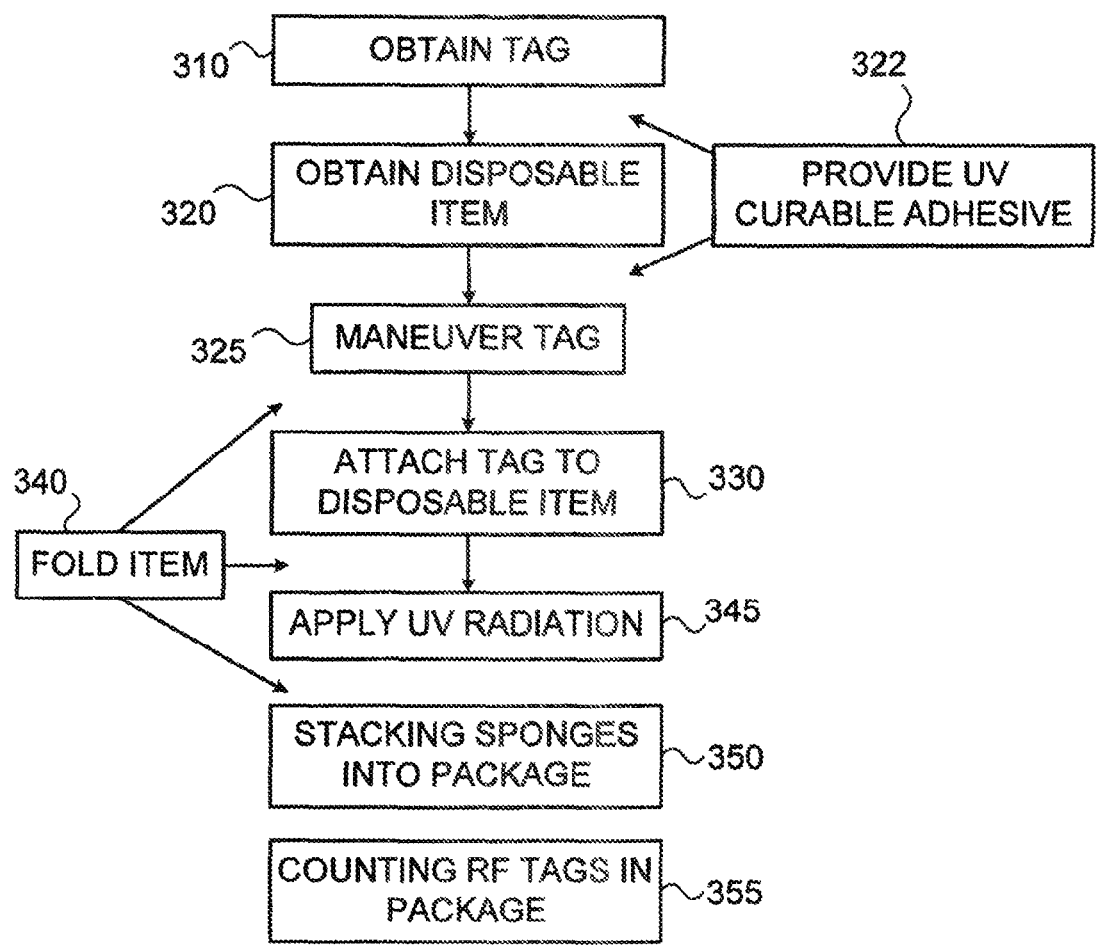
FIG. 3 shows a method for attaching a tag to a disposable item, according to exemplary embodiments of the subject matter.

FIG. 3 shows a method for attaching a tag to a disposable item, according to exemplary embodiments of the subject matter. In step 320, a disposable item is obtained. The disposable item may be obtained from a disposable item storage or from a user. As explained above the disposable item may be a sponge, cotton wool, and the like.

In step 310, a tag is obtained. The tag may contain a transmitting device, sending a signal to a computerized or electronic entity. Such computerized or electronic entity receives signals from one or more items in the environment and provides indications to the user. The tag may contain an RF transmitter or another transmitter that transmits wireless signals to the computerized or electronic entity.

In step 325, the tag is maneuvered from a tag storage to the disposable item. The maneuvering may be performed using a maneuvering mechanism 225. The tag can be held in one or more gripping arms while being maneuvered towards the disposable item. The maneuver can be made to a predefined area in the working plate 230 as shown in FIG. 2.

In step 330, the tag is attached to the disposable item. The attachment may be performed on a predefined area of the disposable item. In some cases, the maneuvering mechanism 225 comprises a control unit for determining the location in which the tag is released from the maneuvering mechanism 225.

In step 322, adhesive material is provided to attach the tag to the disposable item. The adhesive material is curable using ultraviolet radiation. The adhesive material may be, for example, DYMAX Ultra Light-Weld 204-CTH-F. The adhesive material may be provided on the tag. Alternatively, the adhesive material may be provided on the disposable item.

In step 340, the disposable item is folded. The folding may be performed before or after the tag is attached to the disposable item. The folding may be performed by a mechanical or electronic mechanism or by a person. The adhesive material may be in contact with more than one layer of the folded disposable item.

In step 345, ultraviolet radiation is applied on the disposable item attached to the tag. Such ultraviolet radiation may be in an amount of about 50 mW/cm$^2$ or in a range of 50 mW/cm$^2$-10 W/cm$^2$. The ultraviolet radiation may be applied for a duration in a range of 0.5 to 2 seconds in order to cure the adhesive material on the disposable item. In other cases, the amount of ultraviolet radiation depends on the type of the adhesive material. The radiated ultraviolet radiation cures the adhesive material.

In step 350, one or more disposable items are packed into a package for delivery to a hospital or another entity using the disposable items. In step 355, the number of tags in each package are counted to verify the number of disposable items in each package.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:

1. A method of attaching a tag to a disposable item to track the disposable item, the method comprising:
    obtaining a tag;
    obtaining a disposable item to be tracked by the tag;
    placing the disposable item on a working plate in the form of a conveyer belt;
    conveying the disposable item to an attachment point;
    determining a location on the disposable item onto which the tag is released from a maneuvering mechanism for attaching to the disposable item depending on the type of disposable item;
    attaching the tag to the disposable item using an adhesive material;
    applying a pre-determined amount of ultraviolet radiation for a specific duration on the tag attached on the disposable item to cure the adhesive material with the ultraviolet radiation as it passes by an ultraviolet emitting device;
    wherein the pre-determined amount is selected depending on the type of adhesive material;
    packing one or more of the disposable items into a package; and
    counting the number of tags in the package with a tag reader to verify the number of disposable items in the package.

2. The method according to claim 1, further comprises a step of folding the disposable item.

3. The method according to claim 2, wherein the adhesive material, is attached to more than one layer of the folded disposable item.

4. The method according to claim 2, wherein the ultraviolet radiation cures the adhesive material in more than one layer of the folded disposable item.

5. The method according to claim 2, wherein the step of attaching is performed before folding the disposable item.

6. The method according to claim 1, wherein the tag is an RF tag.

7. The method according to claim 1, wherein the adhesive material is attached to the tag before the tag is attached to the disposable item.

8. The method according to claim 1, wherein the adhesive material is attached to the disposable item before the tag is attached to the disposable item.

9. The method according to claim 1, further comprising a step of maneuvering the tag, from a tag storage to the working plate on which the disposable item is mounted.

10. The method according to claim 1, wherein the adhesive material is an UV curable adhesive.

11. A system for attaching a tag to a disposable item, the system comprising:
    a tag storage for storing tags;
    a disposable storage adapted to store disposable items;
    a maneuvering mechanism adapted to maneuver tags towards the disposable items; wherein the maneuvering mechanism includes a control unit for determining a location on the disposable item onto which the tag is released from the maneuvering mechanism depending on the type of disposable item;
    an adhesive material storage unit adapted to provide adhesive material for attaching the tag and the disposable item for tracking the disposable item with the tag;
    an ultraviolet radiation module adapted to apply a pre-determined amount of ultraviolet radiation for a specific duration on the tag attached to the disposable item as it passes by the ultraviolet radiation module;
    wherein the pre-determined amount of ultraviolet radiation is selected depending on the type of adhesive material so that it cures the adhesive material; and
    wherein the system packs one or more of the disposable items into a package and counts the number of tags in the package with a tag reader to verify the number of disposable items in the package.

12. The system according to claim 11, wherein the maneuvering mechanism maneuvers the tag to the adhesive material storage unit before mounting the tag on the disposable item.

* * * * *